United States Patent [19]
Rasmussen

[11] Patent Number: 5,935,837
[45] Date of Patent: Aug. 10, 1999

[54] DNA CONSTRUCTS AND METHODS OF PRODUCING XYLOSE ISOMERASE

[75] Inventor: Michael Dolberg Rasmussen, Vallensbaek, Denmark

[73] Assignee: Novo Nordisk A/S, Bagsvaerd, Denmark

[21] Appl. No.: 08/901,547

[22] Filed: Jul. 28, 1997

[51] Int. Cl.$^6$ ................................ C12N 1/15; C12N 1/21; C12N 9/90; C12N 15/61

[52] U.S. Cl. .................... 435/233; 435/320.1; 435/252.2; 435/252.33; 435/252.35; 435/254.11; 536/23.2

[58] Field of Search ..................................... 435/233, 234, 435/325, 252.3, 254.11, 320.1, 252.33, 252.35, 254.3, 254.6, 254.7; 536/23.2

[56] References Cited

U.S. PATENT DOCUMENTS 5,656,497   8/1997   Zeikus ................................. 536/23.2

*Primary Examiner*—Dian C. Jacobson
*Attorney, Agent, or Firm*—Steve T. Zelson, Esq.; Reza Green, Esq.

[57] ABSTRACT

The present invention relates xylose isomerases obtainable from strains of Thermotoga. More specifically the invention provides DNA sequences encoding xylose isomerases, expression vectors and host cells comprising the DNA sequences of the invention, and methods of producing xylose isomerases. The invention also provides isolated xylose isomerases free from homologous impurities and obtained by the method of the invention.

13 Claims, No Drawings

DNA CONSTRUCTS AND METHODS OF PRODUCING XYLOSE ISOMERASE

TECHNICAL FIELD

The present invention relates xylose isomerases obtainable from strains of Thermotoga. More specifically the invention provides DNA constructs encoding xylose isomerases, expression vectors and host cells comprising the DNA sequences of the invention, and methods of producing xylose isomerases. The invention also provides isolated xylose isomerases free from homologous impurities and obtained by the method of the invention.

BACKGROUND OF THE INVENTION

U.S. Pat. Nos. 5,219,751 and U.S. Pat. No. 5,268,280 disclose glucose isomerases obtained from *Thermotoga maritima* and *Thermotoga neapolitana*. However, these patents do not disclose DNA constructs encoding these enzymes.

Vieille et al., *Appl. Environ. Microbiol.* 1995 61 (5) 1867–1875, describe a gene derived from a strain of *Thermotoga neapolitana*, encoding a xylose isomerase, which gene consists of 444 amino acid residues, and has a calculated molecular weight of 50,892.

SUMMARY OF THE INVENTION

The present invention relates to isolated DNA sequences derived from a strain of Thermotoga encoding a xylose isomerase.

DETAILED DESCRIPTION OF THE INVENTION

DNA Sequences

The present invention provides a DNA sequence encoding a xylose isomerase. As defined herein, a DNA sequence of the invention includes DNA constructs and isolated DNA sequences that has been cloned by procedures usually employed in genetic engineering to relocate a segment of DNA from its natural location to a different site where it will be reproduced. A cloning process usually comprises excision and isolation of the desired DNA segment, insertion a DNA fragment into a vector molecule or recombinant expression vector, and incorporation of the recombinant vector into a cell where multiple copies or clones of the DNA segment will become replicated.

More specifically the present invention provides a DNA sequence encoding a xylose isomerase, which DNA sequence comprises:

(a) the xylose isomerase encoding part of the DNA sequence cloned into plasmid pSJ1678, which plasmid has been transformed into the strain *Escherichia coli* DSM 11475; and/or (b) the DNA sequence shown as SEQ ID NO: 1; and/or (c) a DNA sequence which is at least 85% homologous to the DNA sequences defined in (a) or (b) above.

It is presently believed that the xylose isomerase encoding part of the DNA sequence cloned into plasmid pSJ1678 of *Escherichia coli* DSM 11475 is identical to the xylose isomerase encoding part of the DNA sequence presented in SEQ ID NO:1.

As defined herein, the term "xylose isomerase encoding part of a DNA sequence" refers to the region of the DNA sequence which corresponds to the region which is translated into a polypeptide sequence (translated polypeptide). In the DNA sequence shown in SEQ ID NO: 1 this is the region between the first "ATG" start codon ("AUG" codon in mRNA) and the following stop codon ("TAA", "TAG" or "TGA"). In SEQ ID NO: 1, the DNA sequence encoding the mature xylose isomerase is located in between positions 101 and 1433 (in the sequence listing designated CDS).

The present invention also is directed to a DNA sequence that differs from the xylose isomerase encoding part of the DNA sequence that has been cloned into plasmid pSJ1678, and which plasmid has subsequently been transformed into the strain *Escherichia coli* DSM 11475, or to the DNA sequence shown as SEQ ID NO: 1, by virtue of the degeneracy of the genetic code.

The present invention also is directed to a DNA sequence which encodes a xylose isomerase having the amino acid sequence set forth as the mature part of SEQ ID NO: 2.

The present invention also is directed to homologous DNA sequences. In a preferred embodiment the DNA sequence of the invention is at least 85% homologous, preferably at least 90% homologous, more preferred at least 95% homologous, to the DNA sequence shown as SEQ ID NO: 1.

A homologous DNA sequence of the invention may be constructed on the basis of the DNA sequence shown as SEQ ID NO: 1, e.g. be a sub-sequence thereof. Thus a homologous DNA sequence of the invention may be constructed by introduction of nucleotide substitutions which do not give rise to another amino acid sequence of the xylose isomerase encoded by the DNA sequence, but which correspond to the codon usage of the host organism intended for production of the enzyme.

Alternatively a homologous DNA sequence of the invention may be constructed by the introduction of nucleotide substitutions which may give rise to a different amino acid sequence (i.e. a variant of the xylose isomerase of the invention).

When carrying out nucleotide substitutions, amino acid changes are preferably of a minor nature, i.e. conservative amino acid substitutions that do not significantly affect the folding or activity of the protein, small deletions, typically of one to about 30 amino acids; small amino- or carboxyl-terminal extensions, such as an amino-terminal methionine residue; a small linker peptide of up to about 20–25 residues; or a small extension that facilitates purification, such as a poly-histidine tract; an antigenic epitope or a binding domain.

Examples of conservative substitutions are within the group of basic amino acids, such as arginine, lysine, histidine; acidic amino acids, such as glutamic acid and aspartic acid; polar amino acids, such as glutamine and asparagine; hydrophobic amino acids, such as leucine, isoleucine, valine; aromatic amino acids, such as phenylalanine, tryptophan, tyrosine; and small amino acids, such as glycine, alanine, serine, threonine, methionine (For a general description of nucleotide substitution, see e.g. Ford et al., *Protein Expression and Purification* 1991 2 95–107).

It will be apparent to persons skilled in the art that such substitutions can be made outside the regions critical to the function of the molecule and still result in an active polypeptide. Amino acids essential to the activity of the polypeptide encoded by the DNA sequence of the invention, and therefore preferably not subject to substitution may be identified according to procedures known in the art, such as site-directed mutagenesis or alanine-scanning mutagenesis (cf. e.g. Cunningham and Wells; *Science* 1989 244 1081–1085). In the latter technique, mutations are introduced at every residue in the molecule, and the resultant mutant molecule is tested for biological (i.e. xylose isomerase) activity to identify amino acid residues that are critical to the activity of the molecule. Sites of substrate-enzyme interaction can also be determined by analysis of crystal structure as determined by such techniques as nuclear magnetic resonance analysis, crystallography or photo affinity labeling (cf. e.g. de Vos et al., *Science* 1992 255 306–312; Smith et al., *J. Mol. Biol.* 1992 224 899–904; Wlodaver et al., *FEBS Lett.* 1992 309 59–64).

The DNA sequence of the invention may be of genomic, cDNA, or synthetic origin, or of any combination thereof.

The DNA sequence of the invention can also be cloned by any general method involving:

cloning, in suitable vectors, a cDNA library from any xylose isomerase producing strain;

transforming suitable yeast host cells with said vectors;

culturing the host cells under suitable conditions to express any enzyme of interest encoded by a clone in the cDNA library;

screening for positive clones by determining any xylose isomerase activity of the enzyme produced by such clones; and isolating the enzyme encoding DNA from such clones.

The DNA sequence of the invention may be cloned from the strain *Escherichia coli* DSM 11475 using standard cloning techniques e.g. as described by e.g. Sambrook et al., *Molecular Cloning: A Laboratory Manual*, Cold Spring Harbor, N.Y., 1989.

Alternatively, the DNA of the invention may, in accordance with well-known procedures, conveniently be cloned from any xylose isomerase producing organism by hybridization using a synthetic oligonucleotide probe prepared on the basis of the DNA sequence presented as SEQ ID NO: 1, or any suitable subsequence thereof, or on the basis of the amino acid sequence presented as SEQ ID NO: 2.

Alternatively, the DNA sequence may be cloned by use of PCR primers prepared on the basis of the DNA sequence disclosed herein.

Homologous DNA Sequences

The DNA sequence homology referred to above is determined as the degree of identity between two sequences indicating a derivation of the first sequence from the second.

Homology may suitably be determined by means of computer programs known in the art, such as "GAP" provided in the Program Manual for the Wisconsin Package, Version 8, September 1994, Genetics Computer Group, Wisconsin, USA (Needleman S B and Wunsch C D; *Journal of Molecular Biology* 1970 48 443–453). Using a GAP creation penalty of 5.0 and GAP extension penalty of 0.3, the coding region of the analogous DNA sequences referred to above exhibits a degree of identity preferably of at least 85%, more preferably at least 90%, more preferably at least 95%, most preferably at least 97% with the xylose isomerase encoding part of the DNA sequence shown in SEQ ID NO: 1.

Microbial Sources

The present invention also relates to a DNA sequence which is derived from a strain of Thermotoga. In the context of this invention this term also covers DNA sequences that are obtainable from a strain of Thermotoga, but which have been introduced into a different organism, from which a gene encoding the xylose isomerase may be obtained.

In a more preferred embodiment, the DNA sequence of the invention is derived from a strain of *Thermotoga maritima*, a strain of *Thermotoga elfii*, or a strain of *Thermotoga neapolitana*. In its most preferred embodiment, the DNA sequence of the invention is derived from a strain of *Thermotoga maritima*.

Thermotoga is a well established genus, and type strains are available from various depository authorities. In more preferred embodiment the DNA sequence of the invention is derived from the strain *Thermotoga maritima* DSM 3109, the strain *Thermotoga elfii* DSM 9442 and ATCC 51869, or the strain *Thermotoga neapolitana* DSM 4359 and ATCC 49049.

Recombinant Expression Vectors

In another aspect the invention relates to a recombinant expression vector comprising the DNA sequence of the invention.

The recombinant vector of the invention may be any expression vector which may conveniently be subjected to recombinant DNA procedures, and the choice of vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome, in part or in its entirety, and replicated together with the chromosome(s) into which it has been integrated.

The vector is preferably an expression vector in which the DNA sequence encoding the xylose isomerase is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant expression vector of the invention may further comprise a DNA sequence enabling the vector to replicate in the host cell in question.

The expression vector of the invention may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct the enzyme into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf. e.g. Sambrook et al., op. cit.).

Microbial Host Cells

The DNA sequence of the invention or the recombinant expression vector of the invention comprising the DNA sequence preferably is introduced into a host cell.

The xylose isomerase enzyme, encoded by the DNA sequence of the invention, may be either homologous or heterologous to the host in question. The term "homologous" refers to DNA sequences encoding an enzyme native to the host organism in question. The term "heterologous" refers to DNA sequences that are not naturally expressed by the particular host cell.

Thus, the DNA sequence may be from another organism, or it may be a synthetic sequence. If homologous to the host cell, i.e. produced by the host cell in nature, it will typically be operably connected to another promoter sequence or, if applicable, another secretory signal sequence and/or terminator sequence than in its natural environment.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention include gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, and gram-negative bacteria such as *Echerichia coli*. The transformation of the bacteria may be effected by protoplast transformation, electroporation, conjugation, or by using competent cells in a manner known per se (cf. Sambrook et al., supra).

When expressing the enzyme in a bacteria such as *E. coli*, the enzyme may be retained in the cytoplasm, typically as insoluble granules (known as inclusion bodies), or it may be directed to the periplasmic space by a bacterial secretion sequence. In the former case, the cells are lyzed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacteria such as a strain of Bacillus or a strain of Streptomyces, the enzyme may be retained in the cytoplasm, or it may be directed to the extracellular medium by a bacterial secretion sequence. In the latter case, the enzyme may be recovered from the medium by conventional isolation techniques, as also described below.

Examples of bacterial host cells which on cultivation are capable of producing the enzyme of the invention include fungal host cells such as yeast's and filamentous fungi. In particular, the host cell may be a strain of Trichoderma, in particular a strain of *Trichoderma harzianum* or *Trichoderma reesei*, a strain of Aspergillus, in particular a strain of *Aspergillus oryzae* or *Aspergillus niger*.

Fungal cells may be transformed by a process involving protoplast formation and transformation of the protoplasts followed by regeneration of the cell wall in a manner known per se. The use of Aspergillus as a host microorganism has been described in EP 238 023 (Novo Nordisk A/S).

The host cell may also be a yeast cell, preferably a strain of Saccharomyces, in particular *Saccharomyces cerevisae, Saccharomyces kluyveri* or *Saccharomyces uvarum*, a strain of Schizosaccharomyces sp., in particular *Schizosaccharomyces pombe*, a strain of Hansenula sp., a strain of Pichia sp., a strain of Yarrowia sp., in particular *Yarrowia lipolytica*, or a strain of Kluyveromyces sp., in particular *Kluyveromyces lactis*.

Methods of Producing Xylose Isomerase

In another aspect, the present invention provides a method of producing an isolated or purified xylose isomerase.

As defined herein, an isolated or purified xylose isomerase is a xylose isomerase preparation essentially free of other non-xylose isomerase polypeptides, e.g., at least about 60% pure, preferably about 80% pure, more preferred about 90% pure, and most preferred about 95% pure, as determined by SDS-PAGE.

According to the invention of the invention, a suitable host cell, which has been transformed with a DNA sequence encoding the enzyme, is cultured under conditions permitting the production of the enzyme, and the resulting enzyme is recovered from the culture.

When an expression vector comprising the DNA sequence of the invention is transformed into a heterologous host cell, it is possible to enable heterologous recombinant production of the enzyme of the invention. This makes possible to obtain a highly purified xylose isomerase enzyme composition, characterized by being free from homologous impurities.

As defined herein, homologous impurities covers impurities, in particular polypeptides, originating from the homologous cell from which the DNA sequence of the invention was originally derived.

In the present invention the homologous cell may e.g. be a strain *Thermotoga maritima*, a strain of *Thermotoga elfii* or a strain of *Thermotoga neapolitana*.

The medium used to culture the transformed host cells may be any conventional medium suitable for growing the host cells in question. The expressed xylose isomerase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Industrial Applications

The xylose isomerase obtained by the method of the invention may find application in industrial processes conventionally involving the action of isomerization enzymes, in particular glucose isomerization processes.

By employing the enzyme of the invention in a one-step glucose isomerization process, the reaction temperature may be in the range of from 50 to 130° C.

In another preferred embodiment, the xylose isomerase may be applied in a two step glucose isomerization process. In this process, the first step of the isomerization is carried out as a conventional isomerization process, employing either a conventional isomerization enzyme or the xylose isomerase of the invention, to produce a high fructose syrup containing from about 40 to 50% fructose. In the second step, the end product from the first step is subjected to isomerization at elevated temperatures, i.e. of from 80 to 130° C., and at a pH of from 3.5 to 8, by employing the xylose isomerase of the invention, to produce a high fructose syrup containing from about 50 to 60% fructose.

Other isomerization conditions can be as for conventional isomerization processes. The reaction time can be in the range of 10 seconds to 5 hours, depending on the isomerization temperature, specific activity of the enzyme preparation employed, etc. The isomerization pH affects enzyme activity, stability and by-product formation. The isomerization pH should be in the range of from 3.5 to 8, more preferred 4.5 to 7. By-product formation due to glucose and fructose decomposition increases at higher pH levels.

The feed syrup dry substance content (DS) influences the rate of fructose formation. Too high a DS level results in lower apparent enzyme activity. On the other hand, too dilute a syrup will lead to a lower optimum substrate/enzyme ratio and increased risk of microbial infection. The feed liquor should contain of from 20 to 65%, more preferred 30 to 60% w/w dry substance glucose.

The concentration of monosaccharides in the feed syrup should be as high as possible in order to obtain the maximum isomerization rate. With a low monosaccharide concentration in the feed syrup the isomerization temperature must be elevated in order to attain a given fructose concentration.

For optimal performance of the isomerization process, the xylose isomerase of the invention can be immobilized. The isomerization process of the invention can then be carried out as a continuous, fixed-bed reactor process. In addition to the convenience of continuous operation, the fixed-bed process permits a short reaction time thereby minimizing by-product formation. The enzyme can be immobilized by methods known in the art to produce xylose isomerase preparations with acceptable high unit activities.

EXAMPLES

The invention is further illustrated in the following examples which are not intended to be in any way limiting to the scope of the invention as claimed.

Materials and Methods

Deposited organisms: *Thermotoga maritima* No. DSM 3109 comprises the xylose isomerase encoding DNA sequence of the invention. *Escherichia coli* DSM 11475 containing the plasmid comprising the full length CDNA sequence, coding for the Xylose Isomerase of the invention, in the cloning vector pSJ1678, was deposited by the inventors according to the Budapest Treaty on the International Recognition of the Deposit of Microorganisms for the Purposes of Patent Procedure at Deutsche Sammlung von Mikroorganismen und Zellkulturen GmbH (DSMZ), Mascheroder Weg 1b, DE-3300 Braunschweig, Germany, on Mar. 14, 1997. pSJ1678 was prepared as described in WO 94/19454.

Other strains: Cells of *E. coli* JC411-M3 is mutated in the xylose isomerase gene (Danilevich et al., MGG, 1978, 161, 337–339). Cells were prepared for and transformed by electroporation using a Gene Pulser™ electroporator from BIO-RAD as described by the supplier.

Plasmids: pSJ1678 was prepared as described in WO 94/19454. The strain *Escherichia coli* DSM 11475 containing the plasmid comprising the full length cDNA sequence, coding for the Xylose Isomerase of the invention, in the cloning vector pSJ1678, was deposited by the inventors according to the Budapest Treaty on the International Recognition of the Deposit of Microorganisms for the Purposes of Patent Procedure at Deutsche Sammlung von Mikroorganismen und Zelikulturen GmbH (DSMZ), Mascheroder Weg 1b, DE-3300 Braunschweig, Germany, on Mar. 14 1997.

General molecular biology methods: DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus".

John Wiley and Sons, 1990). Enzymes for DNA manipulations were used according to the specifications of the suppliers.

Genomic DNA preparation: The Thermotoga maritima strain DSM 3109 was propagated anaerobically in a 50 liter fermentor on the medium described in Example 1 of U.S. Pat. No. 5,219,751. Cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

Genomic library construction: Genomic DNA was partially digested with restriction enzyme Sau3A, and size-fractionated by electrophoresis on a 0.7% agarose gel. Fragments between 2 and 7 kb in size were isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298. Isolated DNA fragments were ligated to BamHI digested, alkaline phosphatase treated pSJ1678 DNA, and the ligation mixture transformed into *E. coli* SJ292. Cells were plated on LB agar plates containing 10 μg/ml chloramphenicol and incubated overnight at 37° C.

Identification of positive clones by hybridization: A DNA library in *E. coli,* constructed as described above, was screened by colony hybridization (Sambrook, 1989) using the corresponding nick translation $^{32}$P-labeled PCR product (obtained as described below) as probe. The hybridization was carried out in 2×SSC (Sambrook, 1989), 5×Denhardt's solution (Sambrook, 1989), 0.5% (w/v) SDS, 100 mg/ml denatured salmon sperm DNA for 20 h at 65° C. followed by washes in 5×SSC at 25° C. (2×15 min), 2×SSC, 0.5% SDS at 65° C. (30 min), 0.2×SSC, 0.5% SDS at 65° C. (30 min) and finally in 5×SSC (2×15 min) at 25° C. Positive clones were characterized as described below.

Identification of positive clones by activity: The positive clones were grown in 5 ml TY containing 6 μg/ml Chloramphenicol and incubated overnight at 37° C. Cells were spun down and resuspended in 200 μl of a reaction buffer (50 mM MES (pH 6.0), 10 mM $MgSO_4$, 5% fructose) and sonicated. Cell debris was spun down and the supernatant was tested for xylose isomerase activity by measuring the conversion of fructose to glucose using Haemo-Glucotest 1–44 strips (Boehringer Manheim).

Characterization of positive clones: The positive clones are obtained as single colonies, and plasmids extracted. Phenotypes are confirmed by retransformation, and plasmids characterized by restriction digests, and by DNA sequencing using the chain-termination method (Sanger et al. (1977) Proc. Natl. Acad. Sci. U.S.A. 74:5463–5467) and the Sequenase system (United States Biochemical).

Isolation of the DNA sequence: The Xylose Isomerase encoding part of the DNA sequence shown in SEQ ID NO: 1 coding for the Xylose Isomerase of the invention can be obtained from the deposited organism MOL159 (DSM 11475) by extraction of plasmid DNA by methods known in the art (Sambrook et al. (1989) Molecular cloning: A laboratory manual, Cold Spring Harbor lab., Cold Spring Harbor, N.Y.).

N-terminal amino acid sequencing of the Xylose Isomerase: The enzyme was purified as described in Example 1 of U.S. Pat. No. 5,219,751. N-terminal sequencing was performed by methods known in the art (Findlay et al. (1989) Protein Sequencing: A Practical Approach, IRL Press, Oxford, England). The following amino acid sequence was deduced from the sequencing procedure:

AlaGluPhePheProGluIleProLysIleGlnPheGluGlyLysGluXThr Asn-ProLeuAlaPheArgPheTyrAspProAsn (SEQ ID NO: 2)

where amino acids are described according to the one letter code and X is unknown.

Media: TY and LB agar have been described in EP 0 506 780. TB is 12 g Bacto-tryptone, 24 g Bacto-yeast-extract, 4 ml of 86% Glycerol and 900 ml of water. After autoclaving the broth, 100 ml of autoclaved potassium buffer is added: 0.17 M $KH_2PO_4$, 0.7 M $K_2HPO_4$.

Example 1

Cloning and expression of Xylose Isomerase from *Thermotoga maritima*

Preparation of genomic DNA, library construction, and screening was performed as described in Materials and Methods. One Xylose Isomerase transformant isolated was MOL159 (DSM 11475), containing the plasmid designated pMOL159. pMOL159 is the cloning vector pSJ1678 (see above) containing an insert of approximately 2100 base pairs. This insert was DNA sequenced, and revealed the presence of the Xylose Isomerase gene of the sequence given in SEQ ID NO: 1 in the central part of the insert.

The Primary PCR Product of *Thermotoga maritima*

A primary PCR reaction using two degenerated primers matching two different amino acid sequences of the Xylose Isomerase enzyme were performed on the ligation reaction of the *Thermotoga maritima* gene bank (DSM 3109). One degenerated forward primer (#3086) was constructed according to the amino acid sequenced N-terminal of the Xylose Isomerase as described above, matching amino acid 10–15, the KIQFEG (SEQ ID NO: 2) motif:

AA(A/G) AT(T/C/A) CA(A/G) TT(T/C) GA(A/G) GG (SEQ ID NO: 3), #3086 where the denotion (A/G) corresponds to 50% A and 50% G at the given position in the oligo and (T/C/A) corresponds to 33% T, 33% C and 33% A at the given position.

The amino acid sequence homology between known Xylose Isomerases described by Lee et al., *J. Biol. Chem.* 1990 265 19082–19090, was used to construct the second degenerated reverse primer (#3245) matching amino acid 188–193, the WGGREG (SEQ ID NO: 2) motif:

AA(A/G) AT(A/C/T) CA(A/G) TT(C/T) GA(A/G) GG (SEQ ID NO: 3). #3245

The PCR reaction was performed as follows: 96° C. for 60 seconds; followed by 30 cycles of 94° C. for 10 seconds, 50° C. for 30 seconds, 72° C. for 60 seconds; and one cycle of 72° C. for 5 min.

A PCR fragment of the expected size of 546 base pair was visualized on an 1.5% agarose gel and later used as a probe for colony hybridization of the *Thermotoga maritima* library.

Colony Hybridization of *Thermotoga maritima*

The primary PCR product described above was $^{32}p$ labeled by the Nick Translation procedure described in the Nick translation kit manual by Amersham, Life Technologies. Approximately 5000 colonies were screened by colony hybridization using this probe and a number of clones were identified as positives.

A second colony PCR reaction with the two primers 3086 and 3245 confined the presence of a Xylose Isomerase fragment of 546 base pairs, and the final clone MOL159 was selected for further studies.

Production and Purification of the Xylose Isomerase from MOL159

The Xylose Isomerase clone MOL159 was grown to high density in 1 liter of TB +10 μg/ml of chloramphenicol at 37° C. for 24 hours. The cells were harvested by centrifugation and lyzed in a French press. Cell debris was spun down and the supernatant was used for further purification.

---

What is claimed is:

1. An isolated and purified DNA sequence encoding a xylose isomerase, said DNA sequence comprising the DNA sequence shown as SEQ ID NO: 1.

2. The isolated and purified DNA sequence according to claim 1, wherein said sequence is derived from a strain of Thermotoga.

3. The isolated and purified DNA sequence according to claim 2, wherein said sequence is derived from a strain of *Thermotoga maritima*.

4. The isolated and purified DNA sequence according to claim 3, wherein said sequence is derived from the strain *Thermotoga maritima* DSM 3109.

5. A recombinant expression vector comprising the DNA sequence according to claim 1.

6. A host cell comprising the recombinant expression vector according to claim 5.

7. The host cell according to claim 6, wherein said cell is a bacterial cell.

8. The host cell according to claim 7, wherein said cell is selected from the group consisting of Bacillus, *Echerichia coli,* and Streptomyces.

9. The host cell according to claim 6, wherein said cell is a fungal cell selected from the group consisting of a yeast cell and a filamentous fungal cell.

10. The host cell according to claim 9, wherein said cell is selected from the group consisting of Aspergillus, Fusarium, and Trichoderma.

11. A method of producing a xylose isomerase, which method comprises the steps of (a) culturing a cell according to claim 6 under conditions permitting the production of the enzyme; and (b) recovering the enzyme from the culture.

12. An isolated and purified DNA sequence encoding a xylose isomerase, wherein said xylose isomerase has the amino acid sequence set forth as SEQ ID NO: 2.

13. An isolated and purified DNA sequence encoding a xylose isomerase, said DNA sequence comprising a DNA sequence at least about 97% homologous with the DNA sequence of SEQ ID NO: 1.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 1668 base pairs
       (B) TYPE: nucleic acid
       (C) STRANDEDNESS: single (D) TOPOLOGY: linear (ii) MOLECULE TYPE: DNA (genomic)

(vi) ORIGINAL SOURCE:
        (A) ORGANISM: Thermotoga maritima
        (B) STRAIN: DSM 3109

(ix) FEATURE:
        (A) NAME/KEY: CDS
        (B) LOCATION:101..1433

(xi) SEQUENCE DESCRIPTION: SEQ ID NO: 1:

AACACCTCCC AGATTCAAGT ATATCCTAAA AAAATATTTG AAATGATACC CC AAGATTTT         60

ATATAATTGA TTGATAGAAA AAATTTAGGG AGGTGTTTAC ATG GCA GA A TTT TTC         115

Met Ala Glu Phe Phe
              1             5

CCA GAA ATC CCA AAG ATT CAG TTT GAA GGT AA G GAA AGC ACG AAC CCG         163
Pro Glu Ile Pro Lys Ile Gln Phe Glu Gly Ly s Glu Ser Thr Asn Pro
                10                  15                  20

CTG GCG TTC AGG TTC TAC GAT CCG AAC GAG GT G ATC GAT GGG AAG CCC         211
Leu Ala Phe Arg Phe Tyr Asp Pro Asn Glu Va l Ile Asp Gly Lys Pro
            25                  30                  35

CTC AAG GAT CAT CTG AAG TTT TCC GTC GCC TT C TGG CAC ACT TTC GTG         259
Leu Lys Asp His Leu Lys Phe Ser Val Ala Ph e Trp His Thr Phe Val
        40                  45                  50

AAC GAG GGA AGA GAT CCG TTT GGA GAT CCA AC C GCT GAA CGC CCA TGG         307
Asn Glu Gly Arg Asp Pro Phe Gly Asp Pro Th r Ala Glu Arg Pro Trp
    55                  60                  65

AAC AGG TTC TCC GAT CCC ATG GAC AAA GCT TT T GCA AGG GTG GAC GCT         355
Asn Arg Phe Ser Asp Pro Met Asp Lys Ala Ph e Ala Arg Val Asp Ala
 70                 75                  80
 85

CTC TTC GAG TTC TGC GAA AAG CTC AAC ATC GA G TAC TTC TGT TTC CAC         403
Leu Phe Glu Phe Cys Glu Lys Leu Asn Ile Gl u Tyr Phe Cys Phe His
                90                  95
                100

GAC AGA GAC ATC GCT CCC GAA GGA AAG ACG CT C AGA GAG ACA AAC AAG         451

-continued

```
Asp Arg Asp Ile Ala Pro Glu Gly Lys Thr Le
u Arg Glu Thr Asn Lys
            105
                110
                    115

ATA CTG GAC AAA GTG GTG GAA AGA ATT AAG GA
A AGA ATG AAG GAC AGC           499
Ile Leu Asp Lys Val Val Glu Arg Ile Lys Gl
u Arg Met Lys Asp Ser
        120
            125
                130

AAC GTG AAA CTC CTC TGG GGA ACG GCG AAT CT
G TTC TCC CAC CCG AGG           547
Asn Val Lys Leu Leu Trp Gly Thr Ala Asn Le
u Phe Ser His Pro Arg
    135
        140
            145

TAC ATG CAC GGC GCC GCG ACG ACA TGC AGT GC
G GAT GTC TTT GCC TAC           595
Tyr Met His Gly Ala Ala Thr Thr Cys Ser Al
a Asp Val Phe Ala Tyr
150                 1
55                      1
60                          1
65

GCG GCG GCC CAG GTG AAG AAG GCC CTC GAG AT
C ACA AAA GAA CTA GGA           643
Ala Ala Ala Gln Val Lys Lys Ala Leu Glu Il
e Thr Lys Glu Leu Gly
            170
                175
                    180

GGA GAA GGC TAC GTC TTC TGG GGT GGA AGA GA
A GGC TAT GAA ACA CTC           691
Gly Glu Gly Tyr Val Phe Trp Gly Gly Arg Gl
u Gly Tyr Glu Thr Leu
        185
            190
                195

CTC AAC ACA GAT CTC GGG CTG GAA CTC GAA AA
T CTC GCG AGA TTT CTC           739
Leu Asn Thr Asp Leu Gly Leu Glu Leu Glu As
n Leu Ala Arg Phe Leu
    200
        205
            210

AGA ATG GCA GTG GAG TAC GCA AAG AAG ATC GG
C TTC ACC GGA CAG TTC           787
Arg Met Ala Val Glu Tyr Ala Lys Lys Ile Gl
y Phe Thr Gly Gln Phe
        215
            220
                225

CTC ATA GAA CCC AAG CCG AAA GAA CCC ACC AA
G CAC CAG TAC GAT TTC           835
Leu Ile Glu Pro Lys Pro Lys Glu Pro Thr Ly
s His Gln Tyr Asp Phe
230                 2
35                      2
40                          2
45

GAT GTG GCA ACG GCC TAC GCT TTC CTG AAG AA
C CAC GGC CTT GAT GAG           883
Asp Val Ala Thr Ala Tyr Ala Phe Leu Lys As
n His Gly Leu Asp Glu
            250
                255
                    260
```

```
TAC TTC AAG TTC AAC ATT GAA GCG AAC CAC GC
G ACA CTT GCC GGT CAC        931
Tyr Phe Lys Phe Asn Ile Glu Ala Asn His Al
a Thr Leu Ala Gly His
          265
              270
                  275

ACA TTC CAG CAC GAA CTG AGG ATG GCA AGG AT
C CTC GGA AAA CTT GGA        979
Thr Phe Gln His Glu Leu Arg Met Ala Arg Il
e Leu Gly Lys Leu Gly
          280
              285
                  290

AGC ATC GAC GCC AAC CAG GGA GAT CTC CTG CT
C GGC TGG GAC ACC GAC        1027
Ser Ile Asp Ala Asn Gln Gly Asp Leu Leu Le
u Gly Trp Asp Thr Asp
          295
              300
                  305

CAG TTC CCA ACG AAC ATC TAC GAC ACA ACA CT
T GCC ATG TAC GAA GTG        1075
Gln Phe Pro Thr Asn Ile Tyr Asp Thr Thr Le
u Ala Met Tyr Glu Val
310                                      3
15                                       3
20                                       3
25

ATA AAA GCA GGA GGA TTC ACA AAG GGT GGC CT
C AAC TTC GAC GCG AAG        1123
Ile Lys Ala Gly Gly Phe Thr Lys Gly Gly Le
u Asn Phe Asp Ala Lys
          330
              335
                  340

GTG AGG AGG GCT TCC TAC AAG GTA GAA GAT CT
C TTC ATC GGT CAC ATC        1171
Val Arg Arg Ala Ser Tyr Lys Val Glu Asp Le
u Phe Ile Gly His Ile
          345
              350
                  355

GCA GGA ATG GAC ACC TTC GCC CTC GGC TTC AA
G ATA GCG TAC AAA CTC        1219
Ala Gly Met Asp Thr Phe Ala Leu Gly Phe Ly
s Ile Ala Tyr Lys Leu
          360
              365
                  370

GCG AAA GAC GGA GTG TTC GAC AAG TTC ATC GA
G GAA AAA TAC AGA AGC        1267
Ala Lys Asp Gly Val Phe Asp Lys Phe Ile Gl
u Glu Lys Tyr Arg Ser
          375
              380
                  385

TTC AAA GAA GGT ATC GGA AAA GAG ATC GTA GA
A GGA AAA ACC GAT TTC        1315
Phe Lys Glu Gly Ile Gly Lys Glu Ile Val Gl
u Gly Lys Thr Asp Phe
390                                      3
95                                       4
00                                       4
05

GAA AAA CTC GAA GAG TAT ATA ATA GAC AAA GA
A GAT ATC GAA CTT CCA        1363
Glu Lys Leu Glu Glu Tyr Ile Ile Asp Lys Gl
u Asp Ile Glu Leu Pro
          410
              415
```

420
TCT GGA AAG CAG GAG TAC CTC GAA AGC CTG CT
C AAC AGC TAC ATA GTG      1411
Ser Gly Lys Gln Glu Tyr Leu Glu Ser Leu Le
u Asn Ser Tyr Ile Val
                425
                        430
                                435

AAG ACA ATA GCA GAA CTG AGG T GATGTGGGGT TTGA
GACCCC TTTTCTTGAG      1463
Lys Thr Ile Ala Glu Leu Arg
        440

ACTTCAAAAG TTTCTTCTGC CACTTCTGAT CACGATCGGA ATAATTGTTG TA
GTCGTTGT   1523

ATCCGGACAG AGCGACAGGG TGAAGTTCCC AAAAGGAAGG ATTGTGATCA CA
GATGGTGA   1583

AAAGTCACTC AAACTGGATG TGGAAATAGC GAACACCCCC GCTCTTCGTT CC
ATTGGTCT   1643

GATGTACAGA AAGAGCATCC CGGAC

1668

(2) INFORMATION FOR SEQ ID NO: 2:

(i) SEQUENCE CHARACTERISTICS:
        (A) LENGTH: 444 amino
acids
        (B) TYPE: amino acid
        (D) TOPOLOGY: linear (ii) MOLECULE TYPE: protein (xi) SEQUENCE DESCRIPTION: SEQ
ID NO: 2:

Met Ala Glu Phe Phe Pro Glu Ile Pro Lys Il
e Gln Phe Glu Gly Lys
 1               5
                        10
                                15

Glu Ser Thr Asn Pro Leu Ala Phe Arg Phe Ty
r Asp Pro Asn Glu Val
            20
                    25
                            30

Ile Asp Gly Lys Pro Leu Lys Asp His Leu Ly
s Phe Ser Val Ala Phe
        35
                40
                        45

Trp His Thr Phe Val Asn Glu Gly Arg Asp Pr
o Phe Gly Asp Pro Thr
    50
        55
            60

Ala Glu Arg Pro Trp Asn Arg Phe Ser Asp Pr
o Met Asp Lys Ala Phe
 65
 70
 75
 80

Ala Arg Val Asp Ala Leu Phe Glu Phe Cys Gl
u Lys Leu Asn Ile Glu
            85
                    90
                            95

Tyr Phe Cys Phe His Asp Arg Asp Ile Ala Pr

```
o Glu Gly Lys Thr Leu
        100
            105
                110

Arg Glu Thr Asn Lys Ile Leu Asp Lys Val Va
l Glu Arg Ile Lys Glu
        115
            120
                125

Arg Met Lys Asp Ser Asn Val Lys Leu Leu Tr
p Gly Thr Ala Asn Leu
    130
        135
            140

Phe Ser His Pro Arg Tyr Met His Gly Ala Al
a Thr Thr Cys Ser Ala
145                 1
50                      1
55                          1
60

Asp Val Phe Ala Tyr Ala Ala Ala Gln Val Ly
s Lys Ala Leu Glu Ile
            165
                170
                    175

Thr Lys Glu Leu Gly Gly Glu Gly Tyr Val Ph
e Trp Gly Gly Arg Glu
        180
            185
                190

Gly Tyr Glu Thr Leu Leu Asn Thr Asp Leu Gl
y Leu Glu Leu Glu Asn
    195
        200
            205

Leu Ala Arg Phe Leu Arg Met Ala Val Glu Ty
r Ala Lys Lys Ile Gly
    210
        215
            220

Phe Thr Gly Gln Phe Leu Ile Glu Pro Lys Pr
o Lys Glu Pro Thr Lys
225                     2
30                          2
35                              2
40

His Gln Tyr Asp Phe Asp Val Ala Thr Ala Ty
r Ala Phe Leu Lys Asn
                245
                    250
                        255

His Gly Leu Asp Glu Tyr Phe Lys Phe Asn Il
e Glu Ala Asn His Ala
            260
                265
                    270

Thr Leu Ala Gly His Thr Phe Gln His Glu Le
u Arg Met Ala Arg Ile
        275
            280
                285

Leu Gly Lys Leu Gly Ser Ile Asp Ala Asn Gl
n Gly Asp Leu Leu Leu
    290
        295
            300

Gly Trp Asp Thr Asp Gln Phe Pro Thr Asn Il
```

```
e Tyr Asp Thr Thr Leu
305                   3
10                       3
15                          3
20

Ala Met Tyr Glu Val Ile Lys Ala Gly Gly Ph
e Thr Lys Gly Gly Leu
              325
                 330
                    335

Asn Phe Asp Ala Lys Val Arg Arg Ala Ser Ty
r Lys Val Glu Asp Leu
              340
                 345
                    350

Phe Ile Gly His Ile Ala Gly Met Asp Thr Ph
e Ala Leu Gly Phe Lys
        355
           360
              365

Ile Ala Tyr Lys Leu Ala Lys Asp Gly Val Ph
e Asp Lys Phe Ile Glu
     370
        375
           380

Glu Lys Tyr Arg Ser Phe Lys Glu Gly Ile Gl
y Lys Glu Ile Val Glu
385                   3
90                       3
95                          4
00

Gly Lys Thr Asp Phe Glu Lys Leu Glu Glu Ty
r Ile Ile Asp Lys Glu
              405
                 410
                    415

Asp Ile Glu Leu Pro Ser Gly Lys Gln Glu Ty
r Leu Glu Ser Leu Leu
              420
                 425
                    430

Asn Ser Tyr Ile Val Lys Thr Ile Ala Glu Le
u Arg
        435
           440
```